United States Patent [19]

Wild et al.

[11] Patent Number: 5,081,301
[45] Date of Patent: Jan. 14, 1992

[54] HYDROXYLAMINE DERIVATIVES WHICH ARE INTERMEDIATES FOR MAKING HERBICIDAL COMPOUNDS

[76] Inventors: Jochen Wild, 7 An der Marlach, 6705 Deidesheim; Albrecht Harreus, 13 Teichgasse, 6700 Ludwigshafen; Ulrich Schirmer, 79 Berghalde, 6900 Heidelberg; Norbert Meyer, 22 Dossenheimer Weg, 6802 Ladenburg; Juergen Kast, 24 Kastanienstrasse, 6737 Boehl-Iggelheim; Dieter Kolassa, 8 Moltkestrasse, 6700 Ludwigshafen, all of Fed. Rep. of Germany

[21] Appl. No.: 429,160

[22] Filed: Oct. 30, 1989

[30] Foreign Application Priority Data

Nov. 11, 1988 [DE] Fed. Rep. of Germany ....... 3838310

[51] Int. Cl.$^5$ ........................................ C07C 239/20
[52] U.S. Cl. .................................. 564/300; 548/514
[58] Field of Search ........................................ 564/300

[56] References Cited

FOREIGN PATENT DOCUMENTS 48911 3/1984 European Pat. Off. .
3615473 11/1987 Fed. Rep. of Germany .

OTHER PUBLICATIONS

Dehmlow et al., Phase Transfer Catalysis, Verlas Chemie, Weinheim (1980) pp. 37-45; 86-93.
Organic Reactions, vol. 11, (1960) pp. 189-260.
Organic Reactions, vol. 24 (1976) pp. 225-259.
Dupont et al, Bull. Soc. Chim. France (1954) p. 653.
Morgan et al., J. Med. Chem. vol. 29 (1986) p. 1398.
J. Organic Chemistry, vol. 45 (1980) p. 2566.
J. Am. Chem. Soc., vol. 90 (1968) p. 2882.
Bull. Soc. Chim. France (1961) p. 1849.
J. Organic Chemistry, vol. 37 (1972) p. 922.
J. Med. Chem., vol. 24 (1981) p. 678.
J. of Chem. Ecol., vol. 10 (1984) p. 1201.

*Primary Examiner*—Bernard Dentz
*Attorney, Agent, or Firm*—John H. Shurtleff

[57] ABSTRACT

Hydroxylamine derivatives have the general formula I $$\text{Aryl—A—O—B} \qquad \text{I}$$

where
Aryl is an unsubstituted or substituted, mononuclear or binuclear, isocyclic radical;
A is a 1,4-butenylene group of the general formulae IIa or IIb

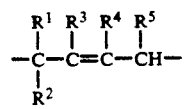

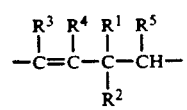

where $R^1$, $R^2$, $R^3$, $R^4$ and $R^5$ are each hydrogen, halogen, $C_1$-$C_6$-alkyl or $C_1$-$C_6$-alkenyl;
B is $NH_2$ or a dicarboximide group of the general formula III

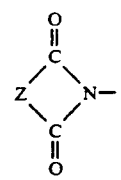

where Z is unsubstituted or substituted phenylene, naphthylene, pyridinylene, cyclopentylene, cyclohexylene, cyclohexenylene, $C_2$-$C_4$-alkenylene or $C_2$-$C_4$-alkylene. The dicarboximides are intermediates for the compounds wherein B is $NH_2$. The latter are used in synthesizing herbicidal compounds.

3 Claims, No Drawings

HYDROXYLAMINE DERIVATIVES WHICH ARE INTERMEDIATES FOR MAKING HERBICIDAL COMPOUNDS

The present invention relates to a hydroxylamine derivative of the general formula I Aryl-A-O-B  I in which Aryl is a mononuclear or dinuclear isocyclic aromatic radical which may be substituted by the following substituents:
up to 5 halogen atoms and/or
up to 3 of the following groups: nitro, nitrile, hydroxyl, amino, $C_1$–$C_7$-monoalkylamino, $C_2$–$C_{14}$-dialkylamino, $C_1$–$C_7$-alkyl, $C_1$–$C_7$-alkoxy, $C_1$–$C_7$-haloalkoxy, $C_1$–$C_7$-haloalkyl, $C_1$–$C_7$-alkylsulfido, $C_1$–$C_7$-haloalkylsulfido, $C_1$–$C_7$-acyl, $C_1$–$C_7$-alkoxycarbonyl, carboxyl, $C_3$–$C_6$-cycloalkyl and or phenyl, A is a 1,4-butenylene group of the general formula IIa or IIb

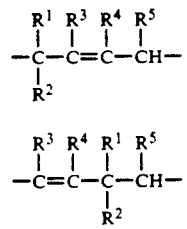

where each of $R^1$ to $R^4$ is hydrogen, halogen, $C_1$–$C_6$-alkyl or $C_1$–$C_6$-alkenyl and $R^5$ is $C_1$–$C_6$-alkyl, and B is either an $NH_2$ group or a dicarboximide group of the general formula III

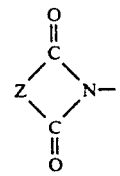

where Z is phenylene, naphthylene, pyridinylene, cyclopentylene, cyclohexylene, cyclohexenylene, $C_2$–$C_4$-alkenylene or $C_1$–$C_4$-alkylene, which may each be unsubstituted or substituted by 1, 2, 3 or 4 halogen, $C_1$–$C_4$-alkyl and/or $C_1$–$C_4$-haloalkyl substituents, and, if B is amino, to salts thereof.

The present invention further relates to the preparation of substituted hydroxylamine derivatives of the general formula I.

EP-B-48,911 describes substituted hydroxylamine derivatives used as starting materials for the preparation of antidiabetics. The large number of compounds claimed in this patent specification formally also includes those of the general formula I, but the description neither discloses how and from which starting materials these compounds can be prepared nor does it give any physical data. The Examples of this patent specification relate only to the preparation of those hydroxylamines where the radical A is propenylene, propoxylene or butylene.

It is an object of the present invention to provide suitable intermediates for preparing herbicides of the general formula VIII

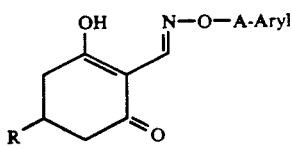

and a method for preparing same.

We have found that this object is achieved by the substituted hydroxylamine derivatives of the general formula I defined at the beginning.

We have also found a process for preparing a substituted hydroxylamine derivative of the general formula I, which comprises reacting a compound of the general formula IV or V

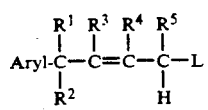

or

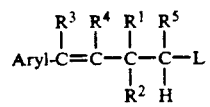

where L is a nucleophilically displaceable leaving group, with a hydroxyimide of the general formula VI

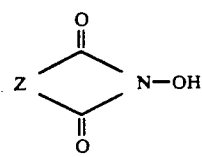

in the presence of a solvent and a base at from 0° to 140° C. and treating the resulting imide ether with a base or an acid to liberate the hydroxylamine derivative I ere B is $NH_2$.

We have further found an embodiment of the process for preparing a substituted hydroxylamine derivative of the general formula Ia

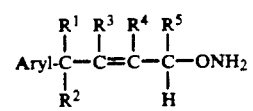

which comprises reacting a compound of the general formula VII

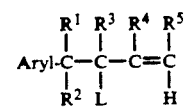

where L is a nucleophilically displaceable leaving group or a mixture of the compound of the general formula VII with the isomeric compound of the general formula IV

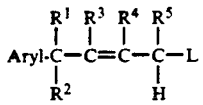

with a hydroxyimide of the general formula VI

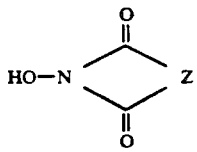

in the presence of a solvent and a base at from 0° to 140° C. and treating the resulting imide ether with an acid or a base to liberate the hydroxylamine derivative Ia.

In the hydroxylamine derivatives of the general formula I according to the invention, aryl is a mononuclear or binuclear, isocyclic aromatic radical, preferably phenyl or naphthyl.

Aryl may be unsubstituted or else substituted by identical or different substituents In general, isocyclic aryl carries from 1 to 5 halogen atoms and/or from 1 to 3 nitro, cyano, hydroxyl, amino, $C_1$–$C_7$-monoalkylamino, $C_2$–$C_{14}$-dialkylamino, $C_1$–$C_7$-alkyl, $C_1$–$C_7$-alkoxy, $C_1$–$C_7$-haloalkyl, $C_1$–$C_7$-haloalkoxy, $C_1$–$C_7$-alkylsulfido, $C_1$–$C_7$-haloalkylsulfido, $C_1$–$C_7$-alkoxycarbonyl, carboxyl, $C_1$–$C_7$-acyl, $C_3$–$C_6$-cycloalkyl and/or phenyl groups.

The halogen on the aryl can be not only fluorine, chlorine or bromine but also iodine, but preferably the aryl is substituted by fluorine, chlorine and/or bromine.

Of the $C_1$–$C_7$-monoalkylamino and $C_2$–$C_{14}$-dialkylamino substituents the $C_1$–$C_{14}$-monoalkylamino and the $C_2$–$C_8$-dialkylamino substituents are preferred. Within these substituents, the alkyl groups bonded to the nitrogen atom can be not only straight-chain but also branched. The alkyl may even be cycloalkyl. Preference is given to monomethylamino, dimethylamino, ethylamino, diethylamino, propylamino, butylamino, tert-butylamino, isobutylamino, hexylamino, cyclohexylamino, dibutylamino, methylhexylamino, methylethylamino, methylcyclohexylamino, cyclopropylamino, cyclopentylamino and heptylamino.

Dialkylamino also covers those groups where the alkyl radical is bonded to the nitrogen to form a ring, for example aziridinyl, pyrrolidinyl or piperidinyl.

The alkyl substituents on the aryl system can be straight-chain, branched or cyclized. Preferred alkyl substituents are $C_1$–$C_4$-alkyl groups, in particular methyl, ethyl, butyl, isopropyl or tert-butyl, but also cyclopropyl, cyclopentyl and cyclohexyl.

Of the $C_1$–$C_7$-alkoxy and $C_1$–$C_7$-alkylsulfido substituents, those of from 1 to 4 carbon atoms are preferred. Particularly suitable substituents are methoxy, ethoxy, propoxy, butoxy, isopropoxy, tert-butoxy, methylsulfido and ethylsulfido.

The $C_1$–$C_7$-haloalkyl, $C_1$–$C_7$-haloalkoxy and $C_1$–$C_7$-haloalkylsulfido substituents can be perhalogenated or else still contain hydrogen. If these substituents are perhalogenated with only one type of halogen, the preferred halogen is fluorine or chlorine, while in the case of perhalogenation with various halogen atoms these groups may also contain bromine as well as fluorine and chlorine. Iodine atoms will in general only be found in those halogenated substituents which additionally contain hydrogen. It will be readily understood that only those halogenated substituents come into consideration which are inert under the conditions of the process for preparing the hydroxylamine derivatives according to the present invention. Preference is given to those substituents which have from 1 to 4 carbon atoms, preferred substituents being: $CF_3$, $CF_2Cl$, $CFCl_2$, $CF_3$—$CF_2$, $C_4H_9$, $CF_2Br$, $CF_3$—$CH_2$, $HCF_2$—$CF_2$, $HCFCl$—$CF_2FCCl_3$, $CF_3$—O, $F_2CCl$—O, $CCl_3$—O, $CF_3$—$CH_2$—O, $HCF_2$—$CF_2$—O, $F_3C$—S.

The aryl groups of the hydroxylamine derivatives according to the present invention may further carry as substituents from 1 to 3 carboxyl groups which may be esterified with a $C_1$–$C_7$-alcohol. Preference is given to those alkoxycarbonyl groups whose alkoxy component has from 1 to 4 carbon atoms.

Suitable substituents also include $C_1$–$C_7$-acyl groups, in particular $C_1$–$C_4$-acyl groups.

Particularly preferred aryl is for example, phenyl, naphthyl, 4-chlorophenyl, 3-chlorophenyl, 2-chlorophenyl, 4-fluorophenyl, 3-fluorophenyl, 2-fluorophenyl, 4-bromophenyl, 3-bromophenyl, 2-bromophenyl, 2,4-difluorophenyl, 2,4-dichlorophenyl, 2,4-dibromophenyl, 3,4-difluorophenyl, 3,4-dichlorophenyl, 3,4-dibromophenyl, 2,3-difluorophenyl, 2,3-chlorophenyl, 2,3-dibromophenyl, 2,5-difluorophenyl, 2,5-dichlorophenyl, 2,5-dibromophenyl, 2,6-difluorophenyl, 2,6-dichlorophenyl, 2,6-dibromophenyl, 3,5-difluorophenyl, 3,5-dichlorophenyl, 3,6-difluorophenyl, 3,6-dibromophenyl, 3,6-dichlorophenyl, 2,4,6-trichlorophenyl, 2-chloro-4-fluorophenyl, 2-bromo-4-fluorophenyl, 3-chloro-4-fluorophenyl, 2-methylphenyl, 3-methylphenyl, 4-methylphenyl, 2,3-dimethylphenyl, 2,4-dimethylphenyl, 2,6-dimethylphenyl, 2,4,6-trimethylphenyl, 4-tert-butylphenyl, 2,6-dimethyl-4-tert-butylphenyl, 2-chloro-4-methylphenyl, 2-nitrophenyl, 3-nitrophenyl, 4-nitrophenyl, 2,4-dinitrophenyl, 2-fluoro-4-nitrophenyl, 2-chloro-4-nitrophenyl, 2-nitro-4-fluorophenyl, 2-nitro-4-chlorophenyl, 2-hydroxy-3-nitrophenyl, 2-hydroxy-4-nitrophenyl, 3-hydroxy-4-nitrophenyl, 2-hydroxyphenyl, 3-hydroxyphenyl, 4-hydroxyphenyl, 2,4-dihydroxyphenyl, 2,5-dihydroxyphenyl, 2,6-dihydroxypheny, 3,5-dihydroxypheny, 3-methyl-4-hydroxyphenyl, 2-methyl-4-hydroxyphenyl, 2-methoxyphenyl, 4-methoxyphenyl, 3-methoxy-4-hydroxyphenyl, 3,4-dimethoxyphenyl, 2-carboxyphenyl, 2-acetylphenyl, 4-acetylphenyl, 2-methoxycarbonylphenyl, 4-methoxycarbonylphenyl, 4-butoxycarbonylphenyl, 2-amino-3-acetylphenyl, 3-methylaminophenyl, 4-methylaminophenyl, 3-N,N-dimethylaminophenyl, 3-cyclopropylaminophenyl, 4-trifluoromethylphenyl, 4-trichloromethylphenyl, 4-monochloromethylphenyl, 4-dichlorofluoromethylphenyl, 4-difluoromethylphenyl, 2-nitrilophenyl, 3-nitrilophenyl or 4-nitrilophenyl.

The radical A of the hydroxylamine derivatives according to the present invention is a butenylene group of the general formula IIa

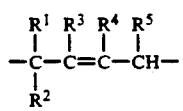

or IIb.

-continued

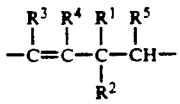

IIb

Accordingly, the double bond of the butenylene group is either conjugated with the aromatic system or separated therefrom by a $CR^1R^2$ group. In the two formulae, $R^1$, $R^2$, $R^3$, $R^4$ and $R^5$ are each hydrogen, halogen, $C_1$-$C_6$-alkyl or $C_1$-$C_6$-alkenyl. Thus, the radical A can be unsubstituted or carry from 1 to 4 identical or different substituents of the type mentioned.

Preferred A is a radical where $R^1$, $R^2$ and $R^5$ are each hydrogen or $C_1$-$C_4$-alkyl and $R^3$ and $R^4$ are each hydrogen, halogen or $C_1$-$C_4$-alkyl.

Preferred halogen substituents of A are fluorine and chlorine, while a particularly preferred alkyl substituent is methyl.

The radical B of the hydroxylamine derivatives according to the present invention is either an amino group or a dicarboximide group of the general formula III

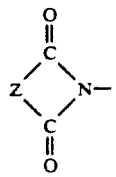

III where Z is phenylene, naphthylene, pyridinylene, cyclopentylene, cyclohexylene, cyclohexenylene, $C_2$-$C_4$-alkenylene or $C_2$-$C_4$-alkylene, which may each be unsubstituted or monosubstituted, disubstituted, trisubstituted or tetrasubstituted by halogen, $C_1$-$C_4$-alkyl and/or $C_1$-$C_4$-haloalkyl.

If Z is a cyclic, aromatic or heteroaromatic radical, it will be readily understood that III is the dicarboximide group of a dicarboxylic acid where the carboxyl groups are in the 1,2-position to each other. Naphthylene thus covers the radicals

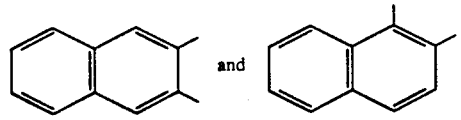

pyridinylene covers the radicals

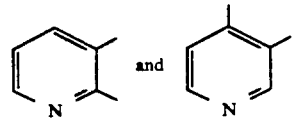

and cyclohexenylene covers the radicals

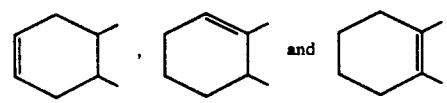

Substituted Z may have any desired substitution pattern. Preference, however, is given to unsubstituted Z.

Particular preference, owing to the ready and inexpensive availability of starting materials, is given to those hydroxylamine derivatives where Z is $C_2$-$C_3$-alkylene, $C_2$-$C_4$-alkenylene or in particular phenylene.

The hydroxylamine derivatives according to the present invention where B is a dicarboximide group are direct intermediates for preparing those hydroxylamine derivatives according to the present invention where B is an amino.

Both those hydroxylamine derivatives where B is a dicarboximide group and those hydroxylamine derivatives which contain a free amino group are stable compounds, and can be isolated, stored and used as such. However, to isolate those hydroxylamine derivatives which contain a free amino group it can prove to be advantageous to convert them into their salts with organic or inorganic acids, since these salts are more readily obtainable in a crystalline form. Furthermore, the choice of the acid anion makes it possible to influence the solubility characteristics of these hydroxylammonium salts in organic solvents or water in an advantageous manner—a measure which facilitates the use of the hydroxylamine derivatives according to the present invention. Particular preference is given to using the hydroxylammonium salts prepared from the corresponding hydroxylamine derivatives with anions such as chloride, bromide, sulfate, nitrate, phosphate, formate, acetate, malonate, oxalate, methanesulfonate, benzenesulfonate or toluenesulfonate.

To prepare the hydroxylamine derivatives Ia

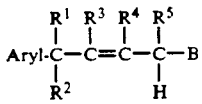

Ia and Ib

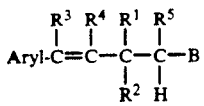

Ib according to the present invention, the starting compounds used are of the general formulae IV

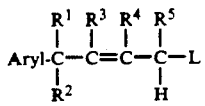

IV

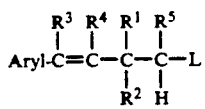

V and VII

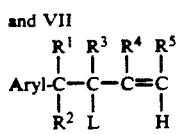

VII where L is a nucleophilically displaceable leaving group. Preferred leaving groups L are the halides chloride, bromide and iodide and the esters of methanesulfonic acid, trifluoromethanesulfonic acid, benzenesulfonic acid, bromobenzenesulfonic acid or toluenesulfonic acid. Particularly preferred leaving groups are the halides chloride and bromide, methanesulfonate and toluenesulfonate.

To prepare the hydroxylamine derivatives according to the present invention where B is a dicarboximide group, the starting compounds of the general formula IV, V and/or VII are reacted with dicarboxylic hydroxyimides of the general formula VI

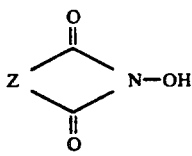

The imide ethers obtained are subsequently converted to the hydroxylamine derivatives according to the present invention where B is amino by elimination of the corresponding dicarboxylic acid radicals.

If the leaving group L is, as in the starting compounds of the general formulae IV and V, in the ω-position relative to the aryl system, its replacement by the hydroxyimide VI is unlikely to be accompanied by an isomerization of the double bond and the products obtained are the corresponding hydroxylamine derivatives Ia and Ib where B is a dicarboximide group. If, by contrast, this reaction is carried out with the isomeric starting compounds of the general formula VII, a virtually quantitative isomerization of the double bond takes place in general in the course of the reaction, leading to hydroxylamine derivatives of the general formula Ia.

This surprising effect is favorable in that it makes it possible to convert mixtures of the isomeric starting compounds IV and VII, as inevitably obtained in the preparation of the starting compounds IV by Meerwein arylation of the corresponding aryl compounds with butadiene, into a uniform product Ia. There is thus no need for an expensive separation of such isomer mixtures.

The reaction of the starting compounds IV, V and/or VII with the hydroxyimides is advantageously carried out in the presence of a base. Any base capable of deprotonating a hydroxyimide VI without attacking the imide system is suitable in principle. This is true in particular of the nonnucleophilic bases. Examples are mineral bases such as alkali metal and alkaline earth metal carbonates, alkali metal and alkaline earth metal bicarbonates, and organic bases such as aliphatic, cycloaliphatic and aromatic tertiary amines. It is also possible to use mixtures of these bases.

Specific examples of the bases are the following compounds: sodium carbonate, potassium carbonate, magnesium carbonate, calcium carbonate, barium carbonate, the bicarbonates of these metals, trimethylamine, triethylamine, tributylamine, ethyldiisopropylamine, N,N-dimethylaniline, 4-N,N-dimethylaminopyridine, diazobicyclooctane, diazobicycloundecane, N-methylpiperidine, 1,4-dimethylpiperazine, pyridine, quinoline, bipyridine and phenanthroline. Preference is given to the inexpensive bases sodium carbonate and potassium carbonate.

The base is in general added in an amount which may range from equivalent to an excess of 5 equivalents, based on the hydroxyimide. A larger excess is possible, but does not bring any additional benefits. The use of a smaller amount of base is likewise possible. Preference, however, is given to using a base amount of from 1 to 3, in particular from 1 to 2, equivalents per hydroxyimide VI.

The use of nucleophilic bases, for example alkali metal and alkaline earth metal hydroxides, in particular sodium hydroxide and potassium hydroxide, is likewise possible. In this case it is advantageous to use the base in an equivalent amount relative to the hydroxyimide VI in order to anticipate a nucleophilic attack of the hydroxyl ions on the carbonyl function of the imide group.

It is advantageous to react the starting compounds IV, V and/or VII with the hydroxyimides VI in a solvent which is inert under the reaction conditions. Advantageous solvents are for example polar aprotic solvents such as dimethylformamide, N-methylpyrrolidone, dimethyl sulfoxide, sulfolane and cyclic ureas. The amount of solvent is in general not critical.

The reaction of the starting compounds IV, V and/or VII with the hydroxyimides VI may also be carried out using phase transfer catalysis. In this case, a water-immiscible solvent, preferably a chlorohydrocarbon, is used. Suitable phase transfer catalysts are the usual quaternary ammonium and phosphonium salts, polyethylene glycols, polyethylene glycol ethers and crown ethers used for such purposes and as described for example in Dehmlow et al., Phase Transfer Catalysis, pages 37–45 and pages 86–93, Verlag Chemie, Weinheim 1980. Phase transfer catalysts are advantageously used in amounts of from 1 to 10% by volume, preferably in amounts of from 3 to 5% by volume, based on the volume of the reaction mixture.

The reaction of the starting compounds IV, V and/or VII with the hydroxyimides VI is in general carried out at from 0° to 140° C., preferably at from 20° to 100° C., in particular at from 40° to 80° C. Advantageously, the reaction is carried out by initially introducing the hydroxyimide VI together with the base in the solvent and to meter the starting material IV, V and/or VII into this solution. It may prove advantageous here to add the hydroxyimide at a lower temperature, for example at from 0° to 50° C., and to heat the reaction mixture to the actual reaction temperature only after this addition.

After the reaction has ended, the cold reaction mixture is advantageously admixed with water, and the hydroxylamine derivative I which is formed, and in which B is a dicarboximide group, separates from the solution as a crystalline solid or as an oil. The hydroxylamine derivatives I obtained in this manner can if desired be further purified by recrystallization or extraction.

The hydroxylamine derivatives I where B is a dicarboximide group can be stored until required or immediately converted into those hydroxylamine derivatives where B is a free amino group. This conversion can be carried out in a conventional manner, as described for example in DE-A 3,615,973 and the references cited therein. Preference is given to using the method of DE-A 3,615,973, whereby the hydroxylamine derivatives I which have a free amino group B are liberated by means of ethanolamine. The liberation of the hydroxylamine derivatives I which have the free amino group B by means of other bases such as aqueous mineral bases, with amines, hydrazines, hydroxylamines or by means of aqueous acids is likewise possible.

The reaction mixtures obtained by these methods can be worked up in a conventional manner, for example by extraction or crystallization, to isolate the hydroxylamine derivatives I which have the free amino group B. To raise the crystallization tendency of these hydroxylamine derivatives, it can frequently be advantageous to convert them into their salts with mineral acids or organic acids. To this end, generally dilute solutions of these acids are reacted with hydroxylamine derivatives, advantageously in equivalent amounts. The resulting hydroxylammonium salts, like the hydroxylamine derivatives which have the free amino group, can be used directly for preparing herbicides of the formula VIII or alternatively, if desired, can be stored.

The starting compounds of the general formulae IV, V and VII are known or preparable by known methods.

For instance, compounds IV and VII can be obtained by Meerwein arylation of the corresponding aromatic diazonium salts with butadiene or appropriately substituted butadienes, the product obtained being a mixture of the isomeric compounds IV and VII in a ratio of 70–80:20–30. Further explanations concerning this method of preparation are given in Organic Reactions 11 (1960), 189–260 and Organic Reactions 24 (1976), 225–259. The double bond in compounds IV and VII prepared by this method has the trans configuration.

The compounds of the general formula IV with the cis-configured double bond can be obtained by the method of Dupont et al. (Bull. Soc. Chim. Fr. (1954), 653) or of Morgan et al. (J. Med. Chem. 29 (1986), 1398).

The starting compounds V with a trans configuration of the double bond are obtainable for example by a Grignard reaction of the aryl halides in question with unsubstituted or $R^1$, $R^2$, $R^3$, $R^4$ or $R^5$-substituted cyclopropanals or cyclopropylalkyl ketones and subsequent dehydration of the resulting cyclopropanecarbinols with simultaneous opening of the cyclopropane ring.

This Grignard reaction can be carried out by standard methods. Suitable dehydrating reagents are of the customary type, such as Brönstedt acids or Lewis acids. Which dehydrating agent is used in a particular case is determined in general by the desired leaving group L which is introduced into the molecule in the course of the dehydration reaction. Suitable dehydrating agents are for example hydrochloric acid, hydrobromic acid, hydroiodic acid, toluenesulfonic acid, methanesulfonic acid, benzenesulfonic acid, bromobenzenesulfonic acid, zinc chloride, zinc bromide, zinc iodide, magnesium bromide, magnesium iodide, phosphorus trichloride, phosphorus pentachloride, phosphoryl chloride, phosphorus tribromide and phosphorus triiodide. The use of the Brönstedt acids mentioned is in general preferred. Via the choice of dehydrating agent it is also possible to introduce any further substituents, in particular chloride, bromide or iodide, into the butenylene group. The phosphorus halides mentioned are in general particularly suitable for this purpose. As for the rest, the dehydration of cyclopropanecarbinols to the corresponding alkenes is known and exemplified for example in the references J. Org. Chem. 45, (1980), 2566; J. Amer. Chem. Soc. 90, (1968), 2882; Bull. Soc. Chim. Fr. (1961), 1849; and J. Org. Chem. 37, (1972), 922.

To prepare those starting compounds V where the double bond is in a cis configuration, it is likewise possible to resort to known methods, as described for example in J. Med. Chem. 24, (1981), 678 and J. Chem. Ecol. 10, (1984), 1201.

The compounds according to the present invention are intermediates for herbicides of the general formula VIII.

EXAMPLES

Examples 1 to 7

Example 1

E-N-(4-Phenyl-2-butenyloxy)phthalimide (1)

78.3 g (0.48 mol) of N-hydroxyphthalimide and 44.2 g (0.32 mol) of potassium carbonate were initially introduced in 480 ml of dry N-methylpyrrolidone. 88.8 g (0.54 mol) of a mixture of isomeric arylbutenyl chlorides IX and X

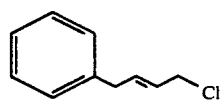

IX

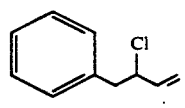

X in an isomer ratio of 78:22 were added dropwise at 40° C. Afterwards the mixture was heated at 60° C. for 6 hours. After cooling, the reaction mixture was poured onto icewater, and the product formed a crystalline precipitate. The product was filtered off with suction, washed and dried.

The same method was used to prepare compounds (2), (3), (4), (5), (6) and (7). The structural formulae, yields and physical data of these compounds are listed in Table 1.

The same method can be used to prepare compounds (8) to (13) listed in Table 2.

TABLE 1

| Compound | Yield | Melting point [°C.] | $^1$H-NMR data: δ(ppm) |
|---|---|---|---|
| (1) [structure shown] | 90% | 70–71 | $^1$H-NMR(DMSO-$d_6$): δ(ppm): 3.35(d, 2H, Ar—CH$_2$), 4.62(d, 2H, CH$_2$—O), 5.4–5.85(m, 1H, Ar—CH$_2$—CH=), 5.85–6.05(m, 1H, =CH—CH$_2$—O), 7.0–7.2(m, 5H, Ar—H), 7.85(s, 4H, phthalimide protons) DMSO-$d_6$: perdeuterated Dimethyl sulfoxide |

TABLE 1-continued

| Compound | Yield | Melting point [°C] | ¹H-NMR data: δ(ppm) |
|---|---|---|---|
| 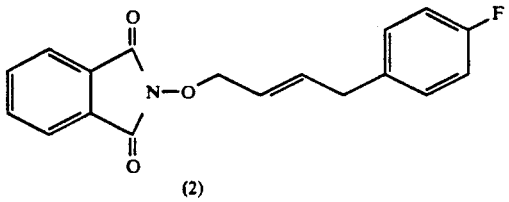 (2) | 85% | 60-62 | in CDCl₃: 3,3(d, 2H, Ar—CH₂); 4.68(d, 2H, —CH₂—O—), 5.7-6,0(m, 2H, —CH=CH—), 6.7-7,1(2d, 4H, Ar—H), 7.7-7,9(m, 4H, phthalimide protons) |
| 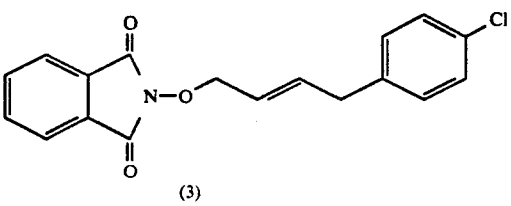 (3) | 83% | 88-91 | in DMSO-d₆: 3,3(d, 2H, Ar—CH₂); 4.6(d, 2H, —CH₂—O—) 5.6-6,0(m, 2H, —CH=CH—), 7.0-7,3(2d, 4H, Ar—H), 7.84(s, 4H, phthalimide protons) |
| 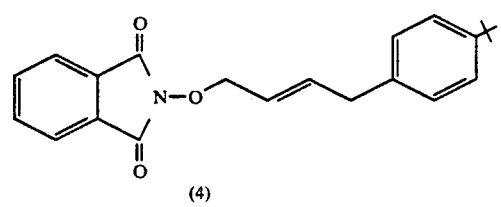 (4) | 85% | Öl | in CDCl₃: 1,2(s, 9H, tert.-Butyl), 3.35(d, 2H, Ar—CH₂—), 4.66(d, 2H, CH₂—O), 5.7-6,0(m, 2H, —CH=CH—), 6.9-7,2(2d, 4H, Ar—H), 7.7-7,9(m, 4H, phthalimide protons) |
| 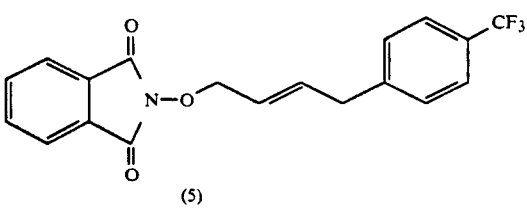 (5) | 91% | 88-89 | in CDCl₃: 3,4(d, 2H, Ar—CH₂), 4.7(d, 2H, —CH₂—O—), 5.7-6,0(m, 2H, —CH=CH—), 7.15-7,2(2d, 4H, Ar—H), 7.7-7,9(m, 4H, Phthalimide Protons) |
| 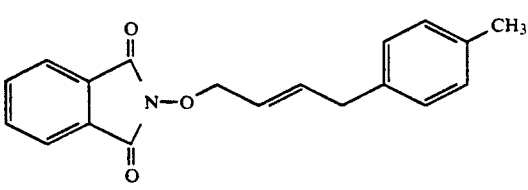 (6) | 33 | 86-87 | in DMSO-d₆: 2,24(s, 3H, —CH₃) 3.28(d, 2H, Ar—CH₂), 4.65(d, 2H, —CH₂—O), 5.6-6,1(2m, 2H, —CH=CH—), 6.95(s, 4H, Ar—H), 7.8(s, 4H, phthalimide protons) |
| 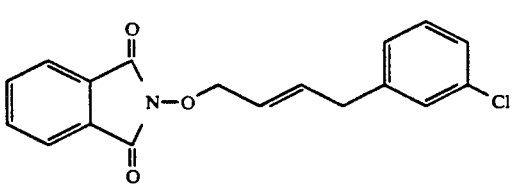 (7) | 98 | 95-97 | in DMSO-d₆: 3.38(d, 2H, Ar—CH₂), 4.65(d, 2H, —CH₂—O—), 5.7-6,1(2m, 2H, —CH=CH—), 6.9-7,3(m, 4H, Ar—H), 7.85(s, 4H, phthalimide protons) |

TABLE 2

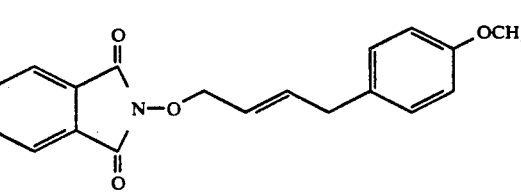 (8)

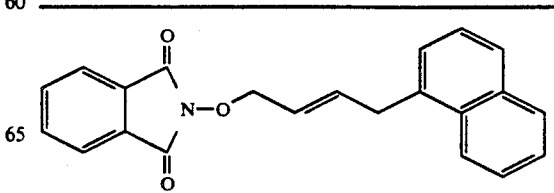 (9)

TABLE 2-continued

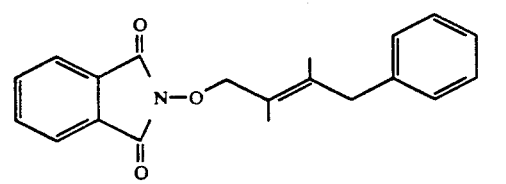
(10)

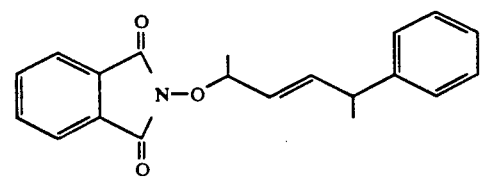
(11)

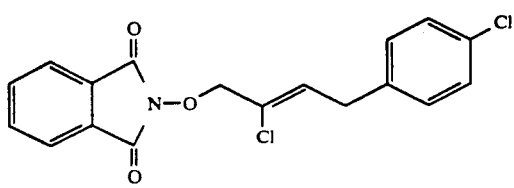
(12)

TABLE 2-continued

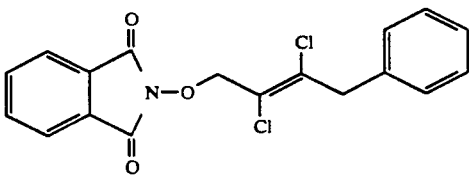
(13)

Examples 8 to 11

Example 11

E-N-(4-Phenyl-3-butenyloxy)phthalimide (14)

Example 1 was repeated to react 67 g (0.32 mol) of E-4-bromo-1-phenyl-1-butene with 29 g of potassium carbonate (0.21 mol) and 51.9 g of N-hydroxyphthalimide (0.32 mol) in 320 ml of N-methylpyrrolidone. The crude product, precipitated by means of ice-water, was taken up in dichloromethane and washed twice with dilute sodium hydroxide solution. A customary working up gives the product in a 56% yield.

The same method was used to obtain compounds (15), (16) and (17) (structural formulae, yields and physical data concerning these compounds: see Table 3).

The same method can be used to obtain compounds (18) to (22) listed in Table 4.

TABLE 3

| Compound | Yield | Melting point [°C.] | $^1$H-NMR data: (ppm) |
|---|---|---|---|
| (14) | 56% | 82–84 | $^1$H-NMR(in CDCl$_3$), δ(ppm):<br>2.7(m, 2H, =CH—CH$_2$),<br>4.3(t, 2H, —CH$_2$—O—),<br>6.2–6,4(m, 1H, =CH—CH$_2$),<br>6.55(d, 1H, Ar—CH=),<br>7.0–7,5(m, 5H, Ar—H),<br>7.6–8,0(m, 4H, phthalimide protons) |
| (15) | 28% | 81–82 | in CDCl$_3$: 2,65(m, 2H, =CH—CH$_2$—),<br>4.28(t, 2H, CH$_2$—O—),<br>6.2–6,7(2m, 2H, —CH=CH—),<br>7.15–7,24(2m, 4H, Ar—H),<br>7.86(s, 4H, phthalimide protons) |
| (16) | 21% | 99–100 | in DMSO-d$_6$: 2,28(s, 3H, CH$_3$),<br>2.62(m, 2H, =CH$_2$—CH$_2$),<br>4.28(t, 2H, —CH$_2$—O—),<br>6.2–6,35(m, 1H, =CH—CH$_2$),<br>6.55(d, 1H, Ar—CH=),<br>7.13+7,28(2d, 4H, Ar—H),<br>7.85(s, 4H, phthalimide protons) |
| (17) | 29% | 94–96 | in CDCl$_3$: 2,65(m, 2H, —CH=CH$_2$—),<br>4.3(t, 2H, —CH$_2$—O—),<br>6.3–6,7(2m, 2H, —CH=CH—),<br>7.4(m, 4H, Ar—H),<br>7.85(s, 4H, phthalimide protons) |

TABLE 4

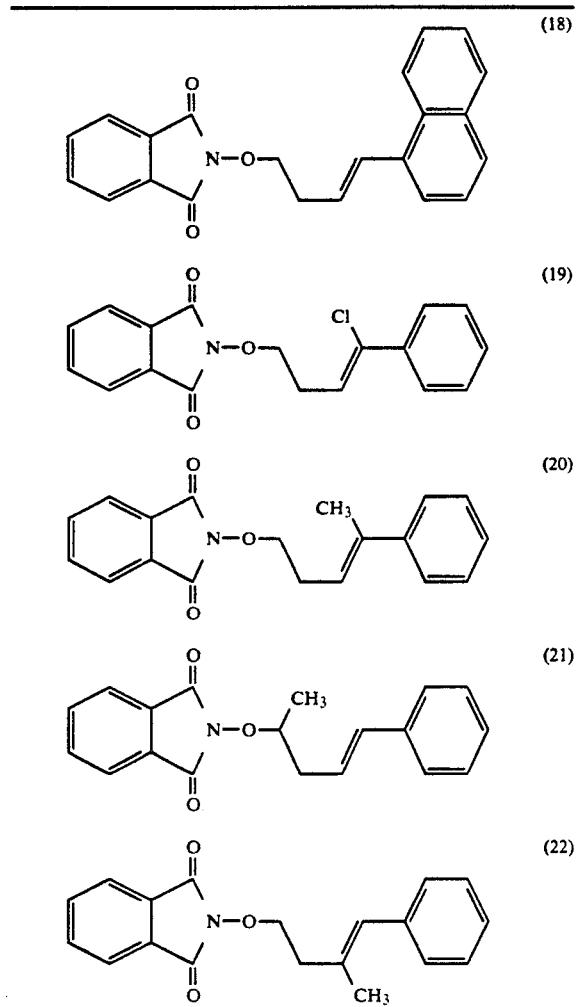

Examples 12 to 19

Example 12

E-4-Phenyl-2-butenyloxyammonium oxalate (23)

55.5 g of compound (1) (0.19 mol) were admixed in 190 ml of ethyl acetate with 11.6 g (0.19 mol) of ethanolamine, and the mixture was stirred at 60° C. for 5 hours. After cooling the solution, precipitated N-(hydroxyethyl)phthalimide was filtered off, and a solution of 18.8 g of oxalic acid (0.21 mol) in 30 ml of ethyl acetate was added to the filtrate. The product crystallized out as oxalate.

The same method was used to prepare compounds (24), (25), (26), (27), (28), (29) and (30) (structural formulae, yields and the physical data concerning these compounds can be found in Table 5). The stoichiometry of the oxalates listed in Table 5 rests on the results of elemental analyses.

The same method can be used to prepare compounds (31) to (34) of Table 6.

Examples 20 to 22

Example 20

E-4-Aminooxy-1-(4-fluorophenyl)-1-butene (35)

85.2 g (0.274 mol) of compound (15) were heated at 60° C. for 2 hours together with 18.4 g (0.3 mol) of ethanolamine in 275 ml of ethyl acetate. After cooling the reaction mixture, precipitated N-(hydroxyethyl)phthalimide was filtered off. The filtrate was admixed with 200 ml of dichloromethane and washed four lines with water. A conventional workup gave the product in a quantitative yield as an oil.

The same method was used to prepare compounds 36 and 37 (structural formulae, yields and NMR data are given in Table 7).

Compounds (38) to (42) of Table 8 can be prepared in a similar manner.

TABLE 5

| Compound | Yield | Melting point [°C.] | $^1$H-NMR data: (ppm) |
|---|---|---|---|
| (23) Ph-CH₂-CH=CH-CH₂-O-NH₂·½(COOH)₂ | 95% | 127-129 | $^1$H-NMR (in DMSO-d$_6$): δ (ppm): 3.25 (d, 2H, Ar—CH$_2$—), 4.18 (d, 2H, CH$_2$—O—), 5.5-5,7 (m, 1H, Ar—CH$_2$—CH=), 5.7-6,0 (m, 1H, =CH—CH$_2$—O), 7.0-7,4 (m, 5H, Ar—H), 9.0 (broad s, 3H, NH$_3^+$) |
| (24) F-C₆H₄-CH₂-CH=CH-CH₂-ONH₂ | 85% | 60-62 | in DMSO-d$_6$: 3,35 (d, 2H, Ar—CH$_2$), 4.2 (d, 2H, CH$_2$—O—), 5.5-5,7 (m, 1H, Ar—CH$_2$—CH=), 5.7-6,0 (m, 1H, =CH—CH$_2$—O), 7.0-7,3 (m, 4H, Ar—H), 9.05 (s, 3H, NH$_3^+$) |
| (25) Cl-C₆H₄-CH₂-CH=CH-CH₂-O-NH₂ | 90% | 114-116 | in DMSO-d$_6$: 3,4 (d, 2H, Ar—CH$_2$), 4.25 (d, 2H, CH$_2$—O), 5.5-6,0 (2m, 2H, —CH=CH—), 7.2-7,4 (2d, 4H, Ar—H), 10.0 (broad s, 4H, NH$_3^+$ + COOH) |

TABLE 5-continued

| Compound | Yield | Melting point [°C.] | ¹H-NMR data: (ppm) |
|---|---|---|---|
| (26) | 80% | 143–146 | in DMSO-$d_6$: 1,12 (s, 9H, tert.-Butyl); 3.35 (d, 2H, Ar—CH$_2$), 4.15 (d, 2H, CH$_2$—O—), 5.5–6,0 (2m, 2H, CH=CH—), 7.0–7,4 (2d, 4H, Ar—H), 7.4–8,0 (broad s, 3H, NH$_3^+$) |
| (27) | 91% | 120–122 | in DMSO-$d_6$: 3,5 (d, 2H, Ar—CH$_2$), 4.22 (d, 2H, CH$_2$—O), 5.5–6,1 (2m, 2H, Ar—CH=CH—), 7.0–7,4 (2d, 4H, Ar—H), 7.7–8,0 (broad s, 3H, NH$_3^+$) |
| (28) | 96% | 115–118 | in DMSO-$d_6$: 2,25 (s, 3H, Ar—CH$_3$) 3.32 (d, 2H, Ar—CH$_2$), 4.22 (d, CH$_2$—O—), 5.5–6,0 (2m, 2H, —CH=CH—), 7.1 (s, 4H, Ar—H), 8.8 (broad S; NH$_3^+$, COOH) |
| (29) | 67% | 99–104 | in DMSO-$d_6$: 3,4 (d, 2H, Ar—CH$_2$), 4.25 (d, 2H, CH$_2$—O), 5.5–6,1 (2m, 2H, —CH=CH—), 7.0–7,5 (m, 4H, Ar—H), 8.1 (broad s, NH$_3^+$, COOH) |
| (30) | 78% | 112–114 | in DMSO-$d_6$: 2,3–2,6 (m, 2H—CH$_2$—CH=); 3.8 (t, 2H, CH$_2$—O—), 6.1–6,4 (m, 1H, =CH—CH$_2$—), 6.5 (d, 1H, Ar—CH=), 7.0–7,5 (m, 5H, Ar—H), 7.8 (broad s, NH$_3^+$ + COOH) |

TABLE 6

(31), (32), (33), (34)

TABLE 7

| Compound | Yield | Melting point [°C.] | ¹H-NMR data: (ppm) |
|---|---|---|---|
| (35) | 98% | öl | ¹H-NMR (in DMSO-$d_6$): δ (ppm): 2.5 (m, 2H, =CH—CH$_2$—) 3.28 (t, 2H, CH$_2$—O), 5.45 (broad s, 2H, —ONH$_2$), 6.0–6,2 (m, 1H, =CH—CH$_2$), 6.22 (d, 1H, Ar—CH=), 6.9–7,4 (2m, 4H, Ar—H) |

TABLE 7-continued

| Compound | Yield | Melting point [°C.] | $^1$H-NMR data: (ppm) |
|---|---|---|---|
| 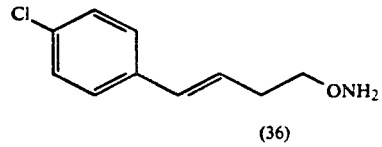 (36) | 92% | öl | in CDCl$_3$: 2,5 (q, 2H, —CH$_2$—CH=), 3.78 (t, 2H, —CH$_2$—O—), 5.4 (broad s, 2H, NH$_2$), 6.1–6,5 (m, 2H, —CH=CH—), 7.1–7,3 (m, 4H, Ar—H) |
| 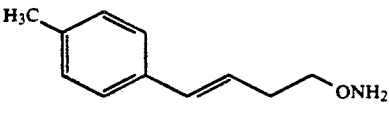 (37) | 98% | öl | in CDCl$_3$: 2,35 (s, 3H, CH$_3$), 2.55 (q, 2H, —CH$_2$—CH=), 3.83 (t, 2H, —CH$_2$—O—), 5.45 (broad s, 2H, NH$_2$), 6.0–6,6 (m, 2H, —CH=CH—), 7.1–7,4 (2d, 4H, Ar—H) |

TABLE 8

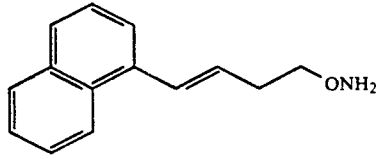 (38)

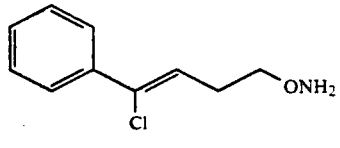 (39)

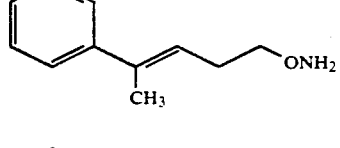 (40)

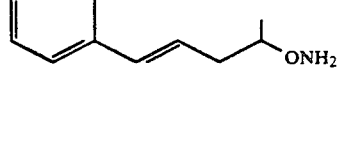 (41)

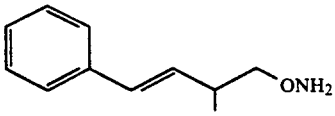 (42)

We claim:
1. A hydroxylamine derivative of the formula

Aryl-A-O-B      I where
Aryl is phenyl or naphthyl substituted by 1 to 5 halogen atoms,
A is a 1,4-butenylene group of the formula $$\begin{matrix} R^3 & R^4 & R^1 & R^5 \\ | & | & | & | \\ -C=C-C-CH- \\ & & | \\ & & R^2 \end{matrix} \quad \text{IIb}$$

where each of $R^1$ to $R^4$ is hydrogen, halogen, $C_2$–$C_6$-alkyl or $C_1$–$C_6$-alkenyl and $R^5$ is hydrogen or $C_1$–$C_6$-alkyl, and
B is the group NH$_2$ or a salt thereof.

2. A substituted hydroxylamine derivative as claimed in claim 1, wherein Aryl is phenyl substituted by fluorine, chlorine or bromine.

3. A substituted hydroxylamine derivative as claimed in claim 1, wherein Aryl is phenyl substituted by chlorine.

* * * * *

UNITED STATES PATENT AND TRADEMARK OFFICE
CERTIFICATE OF CORRECTION

PATENT NO. : 5,081,301
DATED : January 14, 1992
INVENTOR(S) : Wild et al.

It is certified that error appears in the above-identified patent and that said Letters Patent is hereby corrected as shown below:

Column 20,

Claim 1, line 3 from the bottom:

change "$C_2$-$C_6$-alkyl" to --$C_1$-$C_6$-alkyl--; and change "$C_1$-$C_6$-alkenyl" to --$C_2$-$C_6$-alkenyl--.

Signed and Sealed this

Twenty-eighth Day of December, 1993

Attest:

BRUCE LEHMAN

Attesting Officer    Commissioner of Patents and Trademarks